(12) United States Patent
Weiller et al.

(10) Patent No.: US 7,226,530 B2
(45) Date of Patent: Jun. 5, 2007

(54) CONDUCTING POLYMER NANOFIBER SENSORS

(75) Inventors: Bruce H. Weiller, Santa Monica, CA (US); Shabnam Virji, Yorba Linda, CA (US); Richard B. Kaner, Pacific Palisades, CA (US); Jiaxing Huang, Los Angeles, CA (US)

(73) Assignees: The Aerospace Corporation, El Segundo, CA (US); Regents of the University of California, Los Angeles, CA (US)

( * ) Notice: Subject to any disclaimer, the term of this patent is extended or adjusted under 35 U.S.C. 154(b) by 186 days.

(21) Appl. No.: 10/735,078

(22) Filed: Dec. 11, 2003

(65) Prior Publication Data

US 2005/0126909 A1 Jun. 16, 2005

(51) Int. Cl.
*G01N 27/04* (2006.01)
(52) U.S. Cl. .............. 204/400; 422/82.02; 977/953; 977/957
(58) Field of Classification Search ......... 204/400; 422/82.02; 977/953, 957
See application file for complete search history.

(56) References Cited

U.S. PATENT DOCUMENTS

| 4,267,506 A | * | 5/1981 | Shiell | 324/761 |
|---|---|---|---|---|
| 5,130,009 A | * | 7/1992 | Marsoner et al. | 204/403.11 |
| 2003/0137083 A1 | * | 7/2003 | Ko et al. | 264/449 |
| 2003/0217928 A1 | * | 11/2003 | Lin et al. | 205/109 |

OTHER PUBLICATIONS

Briseno et al, Polymer Preprints Aug. 2003, 44(2), p. 140.*
Liu et al, Chemistry A European Journal, Feb. 2003, 9 (3), pp. 604-611.*
Pinto et al, Applied Physics Letters, 83(20), Nov. 2003, pp. 4244-4246.*
Yun et al, Proceedings of SPIE vol. 5220 Nanofabrication Technologies, Aug. 2003, pp. 37-45.*
Reneker et al, Nanotechnology 7 (1996), pp. 216-223.*

* cited by examiner

*Primary Examiner*—Kaj K. Olsen
(74) *Attorney, Agent, or Firm*—Derrick Michael Reid

(57) ABSTRACT

Polymer nanofibers, such as polyaniline nanofibers, with uniform diameters less than 500 nm can be made in bulk quantities through a facile aqueous and organic interfacial polymerization method at ambient conditions. The nanofibers have lengths varying from 500 nm to 10 μm and form interconnected networks in a thin film. Thin film nanofiber sensors can be made of the polyaniline nanofibers having superior performance in both sensitivity and time response to a variety of gas vapors including, acids, bases, redox active vapors, alcohols and volatile organic chemicals.

1 Claim, 6 Drawing Sheets

DOPED POLYANILINE EMERALDINE SALT (σ = 10 S/cm)

DOPED POLYANILINE EMERALDINE SALT ($\sigma$ = 10 S/cm)

DEDOPED POLYANILINE EMERALDINE BASE ($\sigma$ = 1 X $10^{-10}$ S/cm)

METHOD OF SYNTHESIZING POLYANILINE NANOFIBERS

METHOD OF FORMING AN ACID SENSOR

NANOFIBER TIME RESPONSE TO ACID DOPANT

NANOFIBER TIME RESPONSE TO BASE DEDOPANT

METHOD OF FORMING A POLYANILINE NANOFIBER PRECOATED SENSOR

POLYANILINE NANOFIBER PRECOATED SENSOR

CONDUCTING POLYMER NANOFIBER SENSORS

STATEMENT OF GOVERNMENT INTEREST

The invention was made with Government support under contract No. F04701-00-C-0009 by the Department of the Air Force. The Government has certain rights in the invention.

REFERENCE TO RELATED APPLICATIONS

The present application is related to applicant's copending application entitled "Synthetic Method for Conducting Polymer Nanofibers", 10/735,079, filed Dec. 11, 2003, now U.S. Pat. No. 7,144,949 by the same inventors.

FIELD OF THE INVENTION

The invention relates to the field of nanostructured polymers. More particularly, the present invention is related to methods of manufacture of conducting polymer nanofibers and sensors made of conducting polymer nanofibers.

BACKGROUND OF THE INVENTION

Since the discovery that conjugated polymers can be made to conduct electricity through doping, research has been extended in the field of conducting polymer films. Polymers have been made as conducting links of organic monomers having defined chemical structures. Polyaniline can be made as a conducting polymer of aniline monomers. Polyaniline is a unique conjugated polymer in that polyaniline can be tailored for specific applications through a non-redox acid and base doping process. Polyaniline has been studied for electronic and optical applications, such as lightweight battery electrodes, electromagnetic shielding devices, anticorrosion coatings, and sensors. Unlike other conjugated polymers, polyaniline has a simple and reversible acid doping and base dedoping chemistry enabling control over properties of the polyaniline, such as density, solubility, conductivity, and optical absorption. One-dimensional polyaniline nanostructures, including nanowires, nanorods, and nanotubes possess low-dimensional sizes and organic conduction. The electrically conductive form of polyaniline is known as emeraldine having an oxidation state which, when doped with an acid, protonates the imine nitrogens on the polymer backbone and induces charge carriers. The conductivity of polyaniline increases with doping from the undoped insulating emeraldine base form, $\sigma<10^{-10}$ S/cm, to the fully doped, conducting emeraldine salt form, $\sigma>1$ S/cm. Dopants can be added in any desired quantity until all imine nitrogens, that is half of the total nitrogens, are doped, by controlling the pH of the dopant acid solution. Dopants can be removed by interacting the emeraldine salt form with common bases such as ammonium hydroxide.

Conducting polymers can be used in sensors having optical, electrochemical and conducting properties. Conducting polymers are unique by changing properties when chemically treated with oxidizing or reducing agents. After chemical treatment with protonating, deprotonating, oxidizing or reducing agents, the conducting polymer polyaniline can reversibly change from an initially electrically insulating state to a conducting state. This transition can be used in such applications as optical sensors, chemical sensors, and biosensors. Conducting polymers include polyaniline, polypyrole, polythiophene, and their derivatives. Polyaniline is a conducting polymer that is environmentally stable and can react with chemical species at room temperature. As such, polyaniline may be suitable for gas sensing applications using processes that create a uniform thin film of the polyaniline. This thin film may then react with protonating and deprotonating agents to create a conduction pathway that can easily be measured.

The conductivity depends on both the ability to transport charge carriers along the polymer backbone and the ability of the carriers to hop between polymer chains through interpolymer conduction. Any interactions with polyaniline that will alter either of these conduction processes will affect the overall conductivity. This is the underlying chemical property enabling polyaniline to be used as the selective layer in a chemical vapor sensor, such as, a resistance detector generally known as a chemiresistor. Due to room temperature sensitivity, the base of deposition onto a wide variety of sensor substrates and due to the various structures, conducting polymers are potential materials for sensor applications. A polymer chemiresistor would typically consist of a substrate, electrodes, and a conducting polymer selective thin film. Changes in conductivity of the polymer film upon exposure to chemical vapors can be readily monitored with an ohmmeter or electrometer. Polyaniline sensor research has focused on changing the polymer structure to facilitate interaction between vapor molecules and the polymer either by modifying the polymer backbone or the interchain connections. However, poor diffusion can readily outweigh any improvements made to the polymer chains because most of the material other than the limited number of surface sites, is not available for interacting with a chemical vapor, thus degrading sensitivity. One way to enhance diffusion is to reduce film thickness, such as producing monolayers of conventional polymer materials, which leads to a trade-off between sensitivity and robustness. Coating polyaniline on porous substrates can increase the surface area, but the chemistry and physics involving polymer support and polymer electrode interfaces is not well defined for practical use.

Nanostructured polyaniline, such as nanowires, nanofibers, nanotubes, and nanorods may have sufficiently high surface area and faster diffusion rates of gas molecules into the nanostructures for use as chemical sensors with increased sensitivity, as compared to bulk polyaniline. For example, the surface area per unit mass $S_A$ of polyaniline nanofibers increases geometrically as the diameters d of the nanofibers decrease, that is $S_A \sim 1/d$. Even when the thickness of an ultra-thin film is the same as the diameters of the nanofibers, the fibers may outperform a thin film because the fibers have higher surface-to-volume ratios due to their cylindrical morphology. The small diameter of the nanofibers, for example less than 500 nm, coupled with the possibility of gas approaching from all sides should give sensors with improved performance. Despite the high surface area and porosity associated with nanostructures, nanostructured polyaniline has not been used as chemical sensors. This is due to uncertain nanostructure characterization as well as the lack of reliable methods to make high quality polyaniline nanofibers, and reliable methods to coat surfaces with polyaniline nanofibers. No practical nanostructured conducting polymer sensors are available due to the lack of reliable methods for making high quality conducting polymer nanostructures in bulk quantities and the unknown properties of nanofiber characterization.

Syntheses of polyaniline nanostructures have been carried out both chemically and electrochemically by polymerizing the aniline monomers with the aid of either a hard template or a soft template. Examples of hard templates include zeolite channels, track-etched polycarbonate, nanoporous membranes, and anodized alumina. Examples of soft templates for self-assembly of functional polymers include surfactants, polyelectrolytes, or complex organic dopants, such as micelles, liquid crystals, thiolated cyclodextrins, and polyacids, that may be capable of directing the growth of polyaniline one-dimensional nanostructures with diameters smaller than 500 nm. Adding structural directing molecules such as surfactants or polyelectrolytes to the chemical polymerization bath is one way to obtain polyaniline nanostructures. When organic dopants with surfactant functionalities are used, emulsions or micelles can be formed leading to microtube, microfiber, or microrod structures. However, when polyaniline nanostructures with diameters of less than 500 nm are desired, then very complex dopants with bulky side groups are needed, such as sulfonated naphthalene derivatives, fullerenes, or dendrimers.

The formation of polyaniline nanostructures disadvantageously relies either on guidance from hard templates or self-assembled soft templates. These templates disadvantageously use complex synthetic conditions that require the removal of such templates and hence provide low yields and with poor reproducibility. Chemical methods of making polyaniline nanostructures, such as nanotubes, nanofibers, nanowires, and nanorods, disadvantageously require specific structure-directing template materials added into or applied to the polymerization bath. The synthetic conditions disadvantageously have to be carefully designed to accommodate formation and purification to obtain pure polyaniline nanostructures. These template methods are disadvantageously dependent on either a template or a specific complex chemical reagent, and post-synthetic treatments are needed to remove the reagent from the byproducts in order to recover pure nanostructured polyaniline. Therefore, developing synthetic production methods that do not rely on templates, structural directing molecules, or specific dopants is desirable, especially for scaling up to produce large quantities of nanostructured materials suitable for mass usage in chemical sensors.

Electrochemical polymerization and physical methods, such as electrospinning and mechanical stretching can produce conducting polymer nanofibers without templates, but these conducting polymer nanofiber materials can only be made on carefully prepared surfaces offering limited production scaling. Electrochemical synthesis of polyaniline has indicated that some nanofibers form naturally on a synthesis surface while the underlayer is much more compact with microfiber polymers. For the production of polyaniline nanofiber sensors in quantity, there exists a need for a practical bulk synthetic method. Despite the variety of current synthetic methods available to produce polyaniline nanostructures, there is a need for a practical synthetic method capable of making pure, uniform, and template-free polyaniline nanostructures with predetermined small diameters and in bulk quantities. Current synthetic methods are not useful in mass production of ultra-small, low-dimensional structures, such as sensors, using conductive polymer nanofibers of polyaniline. These and other disadvantages are solved or reduced using the present invention.

SUMMARY OF THE INVENTION

An object of the invention is to provide a method for forming a conductive polymer.

Another object of the invention is to provide a method for forming conductive polymer nanofibers.

Another object of the invention is to provide a method for forming conductive polymer nanofibers with predetermined diameters.

Yet another object of the invention is to provide a method for forming conductive polymer polyaniline nanofibers.

A further object of the invention is to provide a method for forming and purifying conductive polymer polyaniline nanofibers in a polymerization bath suitable for production scaling in bulk quantities.

Still another object of the invention is to provide chemical sensors made from conductive polymer polyaniline nanofibers.

Yet a further object of the invention is to provide chemical sensors made from conductive polymer polyaniline nanofibers having strong adherence to conducting terminals.

The invention is direct d towards methods for producing conducting polymer nanofibers and chemical sensors made of conducting polymer nanofibers. In a preferred form, conducting polyaniline nanofibers are produced in a polymerization bath, suitable for batch bulk production and suitable for making a variety of chemical sensors. Polyaniline nanofibers can be doped with an acid and dedoped using a base, in a reversible chemical process. Discovery is made that nanostructured polyaniline has greater sensitivity and faster chemical time responses than the bulk form due to higher effective surface areas and shorter penetration diffusion depths for gas molecules. Discovery is further made that a thiol film on the gold terminals adheres to polyaniline nanofibers for securing a nanofiber polyaniline thin film to a gold conductor. Discovery is further made that polyaniline nanofibers, having diameters less than 500 nm and lengths less than 10 μm, in a thin film have sufficient conductivity changes in response to dopants and dedopants to be suitable for use in chemical sensors. Discovery is also made that selective acids used during polymerization of the polyaniline nanofibers predetermine the resulting diameter of the nanofibers. In the preferred form, an acid and base chemical vapor sensor can be made using conventional gold sensor terminals covered by a polyaniline nanofiber thin film.

In the preferred form, polyaniline nanofibers can be uniformly produced with predetermined diameter sized nanofibers having predetermined lengths in a normal distribution. During polymerization, a selected acid is used to efficiently facilitate the polymerization process, which is selected to predetermine a normal distribution of diameters of the product polymer nanofibers. Each different diameter nanofiber has a resulting different chemical response, and hence, the polymerization process can be tailored to specific performances of the chemical sensors. These polyaniline nanofibers can then be used in a variety of chemical sensors, such as acids, bases, alcohols, volatile organic chemicals and reducing agents. The resulting thin film sensors made of the nanofibers have superior performance in both sensitivity and time response to a variety of gas vapors. Exemplar acids include hydrochloric acid, sulfuric acid, nitric acid, perchloric acid, and camphorsulfonic acid. Exemplar bases include ammonia and butylamine. Exemplar alcohols include methanol, ethanol, and propanol. Exemplar volatile organic chemicals include chloroform and nitromethane. Exemplar reducing agents include hydrazine.

In the general form, polymer nanofibers can change physical properties such as conductivity, density, conformation, oxidation state, and optical absorption, among others, offering a wide variety of sensors for sensing various materials. Polyaniline nanofibers with uniform diameters have predetermined response characteristics. The polyaniline nanofibers can be made in bulk quantities through a facile aqueous and organic interfacial polymerization method at ambient conditions. The nanofibers have varying lengths within a normal distribution and form interconnected networks as a thin film of polyaniline. In the general form, the invention is directed to a synthesis method for producing polymer nanofibers well suited for use in chemical sensors. In the preferred form, the method is suitable for bulk production of polyaniline nanofibers for use in acid and base chemical sensors. The synthesis method is preferably applied to organic monomers that can be linked into conducting polymers, such as polyaniline, polypyrrole, polythiophene and their derivatives. A template-free process using an aqueous polymerization bath provides a practical bulk synthetic method capable of producing bulk quantities of pure and uniform nanofibers with small predetermined diameters. The synthesis method is based on chemical oxidative polymerization of the monomers. The polymerization process is perfected in an immiscible, organic-aqueous, two-phase system. The synthetic method yields polymer nanofibers with nearly uniform reproducible diameters. These and other advantages will become more apparent from the following detailed description of the preferred embodiment.

DETAILED DESCRIPTION OF THE PREFERRED EMBODIMENT

Figure 1A:
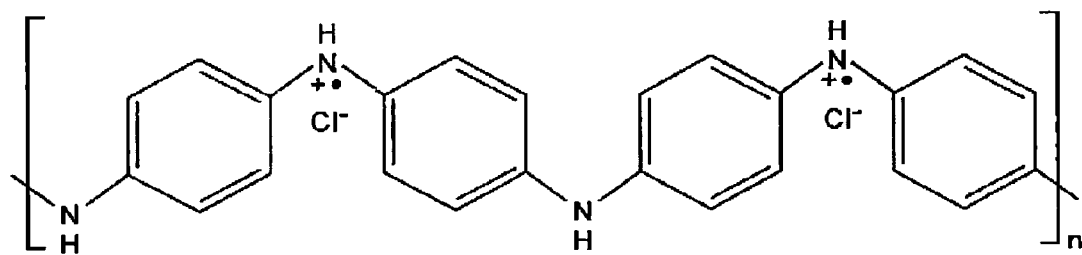
FIG. 1A is a chemical diagram of doped polyaniline emeraldine salt.
Figure 1B:
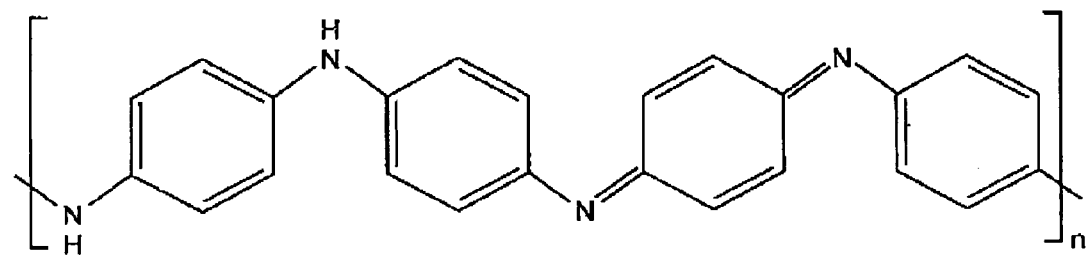
FIG. 1B is a chemical diagram of undoped polyaniline emeraldine base.

An embodiment of the invention is described with reference to the figures using reference designations as shown in the figures. Referring to FIGS. 1A and 1B, monomers, such as aniline monomers can be linked together to form polyaniline. The polyaniline can be doped with an acid, such as hydrochloric acid HCl dopant, as shown in FIG. 1A, and can be dedoped with a base, such as, ammonia $NH_3$.

Figure 2:
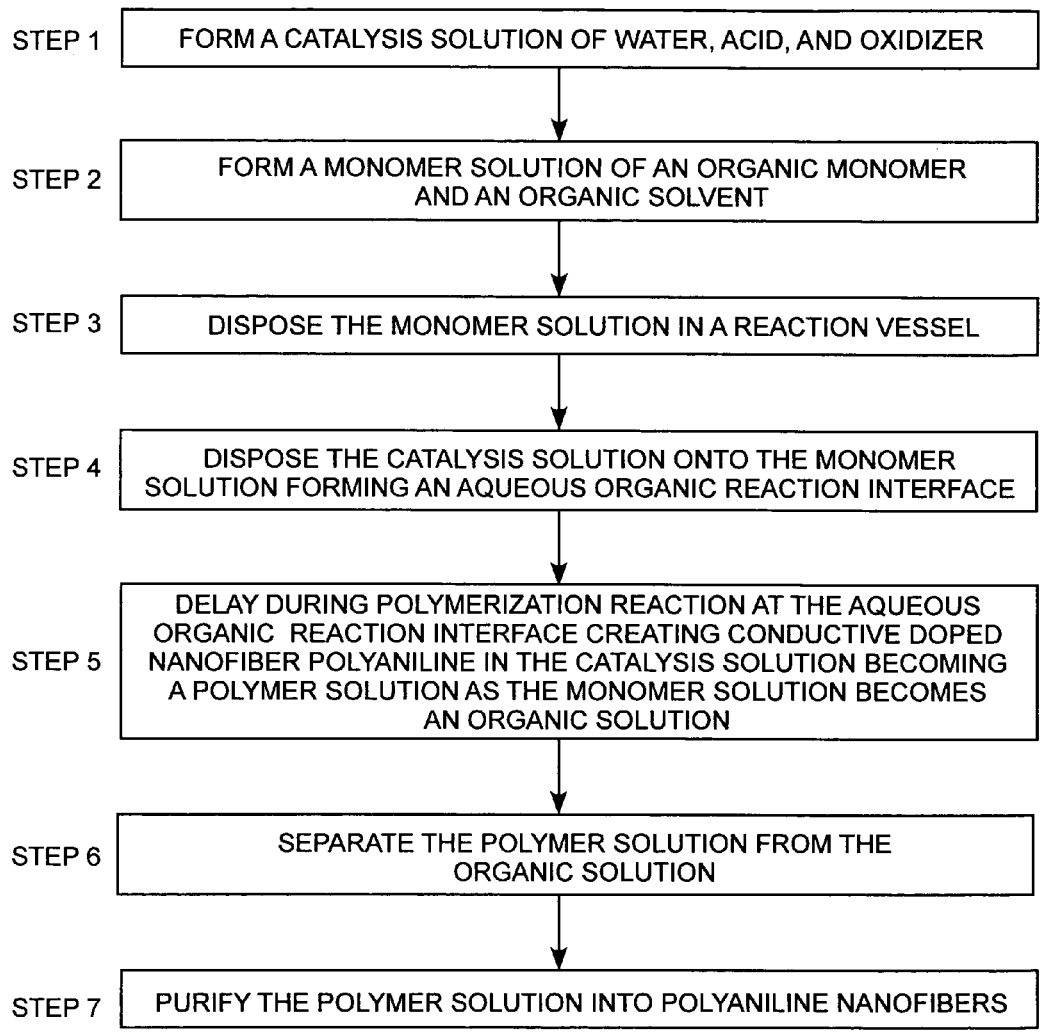
FIG. 2 is a process flow of a method for synthesizing polyaniline nanofibers.

Referring to FIGS. 1A, 1B, and 2, and more particularly to FIG. 2, a seven-step method of synthesizing polyaniline nanofibers relies on a facile chemical process to produce high quality polyaniline nanofibers under ambient conditions using an aqueous-organic interfacial polymerization.

In step 1, a catalysis solution is first formed from water, an acid, and an oxidizer. The acid is preferably hydrochloric acid HCl. but other acids may be used, such as sulfuric acid $H_2SO_4$, nitric acid $HNO_3$, perchloric acid $HClO_4$, phosphoric acid $H_3PO_4$, acetic acid $CH_3COOH$, formic acid HCOOH, tartaric acid $C_4H_6O_6$, methanesulfonic acid $CH_4SO_3$, ethylsulfonic acid $C_2H_7SO_3$, 4-toluenesulfonic acid $C_7H_8SO_3$, and camphorsulfonic acid (CSA). The oxidizer is preferably ammonium peroxydisulfate $(NH_4)_2S_2O_8$, but other oxidizers may be used, such as iron chloride $FeCl_3$ and other peroxydisulfate derivates such as $Na_2S_2O_8$ and $K_2S_2O_8$. In step 2, a monomer solution is formed from a solution of a nonconducting monomer and an organic solvent. In the preferred form, the monomer is aniline, but other carbon-based organic monomers can be used, such as pyrrole, thiophene, toluidine anisidine and other derivatives of aniline such as methylaniline, ethylaniline, 2-alkoxyaniline, and 2,5-dialkoxyaniline monomers, for forming polyaniline, polypyrrole, polythiophene, polytoluidine, polyanisidine, polymethylaniline, polyethylaniline, poly(2-alkoxyaniline) and poly(2,5-dialkOxyaniline) respectively. The organic solvent is preferably carbon tetrachioride $(CCl_4)$, but other organic solvents may be used, such as benzene, toluene, chloroform, methylene chloride, xylene, hexane, diethylether, dichloromethane and carbon disufide. In the preferred form, aniline monomers are dissolved in carbon tetrachioride $(CCl_4)$. In the preferred form, the monomer is aniline, but other carbon-based organic monomers can be used, such as pyrrole, thiophene, toluidine, anisidine and other derivatives of aniline such as methylaniline, ethylaniline, 2-alkoxyaniline, and 2,5 dialkoxyaniline monomers, for forming polyaniline, polypyrrole, polythiophene, polytoluidine, polyanisidine, polymethylaniline, polyethylaniline, poly2-alkoxyanilines and poly2,5-dialkoxyanilines respectively. The organic solvent is preferably carbon tetrachloride $(CCl_4)$, but other organic solvents may be used, such as benzene, toluene, chloroform, methylene chloride, xylene, hexane, diethylether, dichloromethane and carbon disufide. In the preferred form, aniline monomers are dissolved in carbon tetrachloride $(CCl_4)$.

In step 3, the monomer solution is disposed in a reaction vessel that can be scaled from small to large for increased batch production of bulk polymer nanofibers. In step 4, the catalysis solution is disposed nonturbulently into the reaction vessel and onto the monomer solution forming a bifurcated mixture having an aqueous organic reaction interface between the lower monomer solution and the upper floating catalysis solution. In step 5, a polymerization reaction occurs at the aqueous organic reaction interface creating conductive doped nanofiber polyaniline forming in the upper aqueous catalysis solution. The catalysis solution becomes a polymer solution comprising polymers of linked monomers from the monomer solution. As the catalysis solution becomes a polymer solution, the monomer solution is depleted of monomers and becomes an organic solution. Aniline polymerizes at the interface between the bottom organic monomer solution containing dissolved aniline and the upper aqueous catalysis solution containing the oxidant and dopant. As the polymerization reaction proceeds, polyaniline nanofibers form across the interface, slowly diffusing and dispersing into the upper aqueous catalysis solution and eventually filling the upper aqueous solution with dissolved polyaniline nanofibers. At the same time, the color of the lower organic layer turns red-orange due to the formation of by-products, such as aniline oligomers. The nanofiber product in the upper organic solution is then collected and purified by conventional processes such as either dialysis or filtration, yielding a nanofiber product in the form of a water dispersion or a powder, respectively. Further washing or dialyzing with water yields pure, doped polyaniline, which can be dedoped by washing or dialyzing with a base, such as aqueous ammonia. High quality polyaniline nanofibers with dopants ranging from mineral acids to organic acids can be made. The synthesis is readily scalable and can be carried out at room temperature.

In step 6, the polymer solution of polymers is separated from the organic solution. This may be accomplished by siphoning off the top floating polymer solution, and then disposing of the spent organic solution. In step 7, the polymer solution is purified into polyaniline nanofibers. The purification step 7 can be accomplished by conventional filtration or dialysis methods to effectively extract the polymer nanofibers from the polymer solution. For example, the purification can be by dialysis of the colloidal suspension using standard commercially available dialysis membranes.

The polymer nanofibers are preferably conducting polymer nanofibers having predetermined sizes, reactions, and sensitivities to predetermined chemical vapors. The nanofibers have nearly uniform predetermined diameters dependent upon the specific acid used in the catalysis solution. The acidic anion has a predetermined size, which when bound to the nanofiber polymer backbone, affect the overall diameter size of the nanofiber, having typical sizes mostly between 20 and 150 nm and less than 500 nm. For example, hydrochloric acid produces polyaniline nanofibers with a 30 nm diameter distribution, CSA acid produces polyaniline nanofibers with a 50 nm diameter distribution, and perchloric acid produces polyaniline nanofibers with a 120 nm diameter distribution, all with lengths varying from 500 nm to 5 µm. In the general form, the nanofibers have diameters that are less than 500 nm and lengths less than 10 µm.

Gram scale beaker production to kilogram scale vat production can be used to synthesize various quantities of production polymer nanofibers. The nanofibers are typically twisted together forming an interlocking network or mesh of nanofibers. That is, the nanofibers tend to agglomerate into interconnected nanofiber networks, rather than bundles. Doping and dedoping does not affect the fibrillar morphology. As such, the networks of nanofibers have improved sensitivities, are durable for repeated use, and are well suited for thin film deposition on sensor terminals. The nanofibers can then be thin film deposited onto conducting terminals on an insulating substrate to form a sensor.

Figure 3:
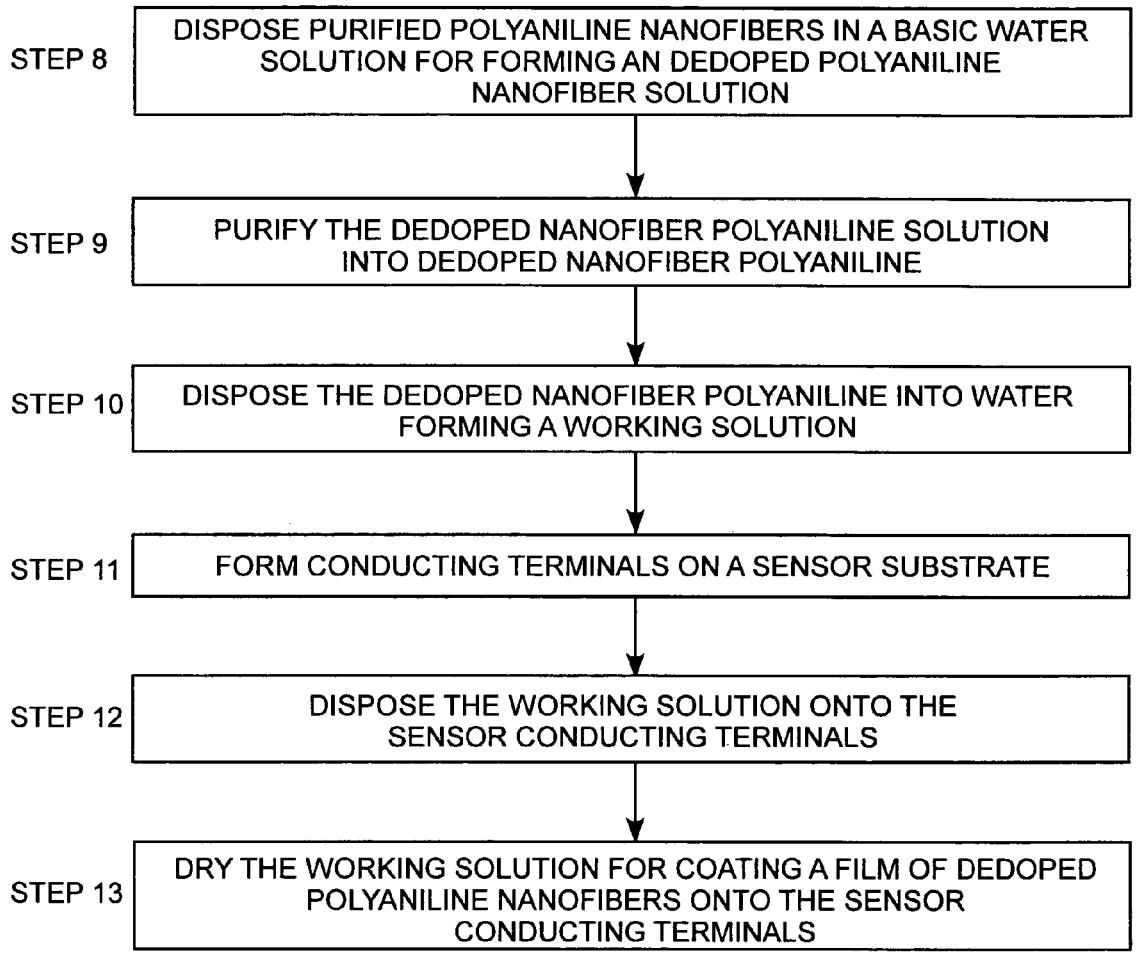
FIG. 3 is a process flow of a method for forming an acid sensor.

Referring to FIGS. 1A, 1B, 2, and 3, and more particularly to FIG. 3, an acid chemical sensor can be made using polyaniline nanofibers when a method of forming an acid sensor having steps 8–13. In step 8, purified polyaniline nanofibers are disposed in a basic water solution for forming an undoped polyaniline nanofiber solution. Discovery is made that polyaniline nanofibers are stable in water, and can be rapidly dedoped in water using a basic solution. In step 9, the dedoped nanofiber polyaniline fibers are purified into a mass of dedoped nanofiber polyaniline. In step 10, the dedoped nanofiber polyaniline is disposed into water for forming a working solution.

In step 11, the conducting terminals are formed on a sensor substrate. The sensor substrate can be made of an insulating material such as glass or quartz. The sensor terminals can be made of a conducting material such as semiconductors and conductors including gold, silver, platinum, polysilicon and doped photoresist. In step 12, the working solution is disposed onto sensor conducting terminals for coating the terminals with the nanofibers. This coating step can be accomplished by conventional coating methods such as spin coating, drop coating, spray coating, and photolithography masked deposition coating. In step 13, the working solution is dried for coating a film of dedoped polyaniline nanofibers onto the sensor conducting terminals. The nanofibers will then react to the presence of various chemicals and solutions, such as an acid causing a change in conductivity that can be sensed at the sensor terminals.

Figure 4A:
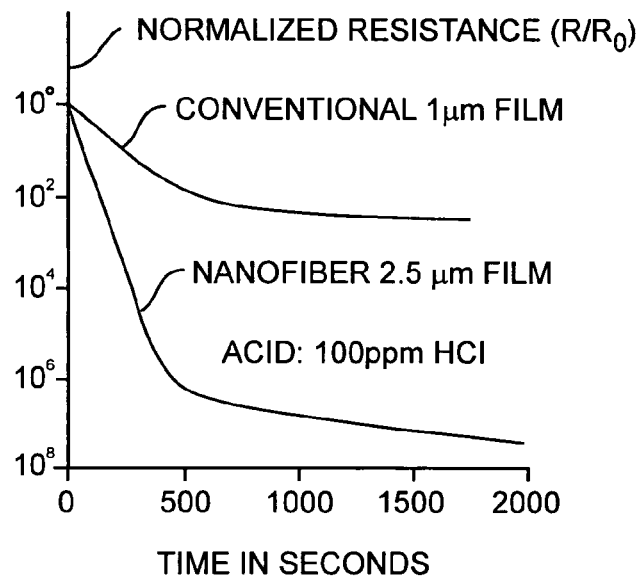
FIG. 4A is a graph of polyaniline nanofiber time response to an acid dopant.
Figure 4B:
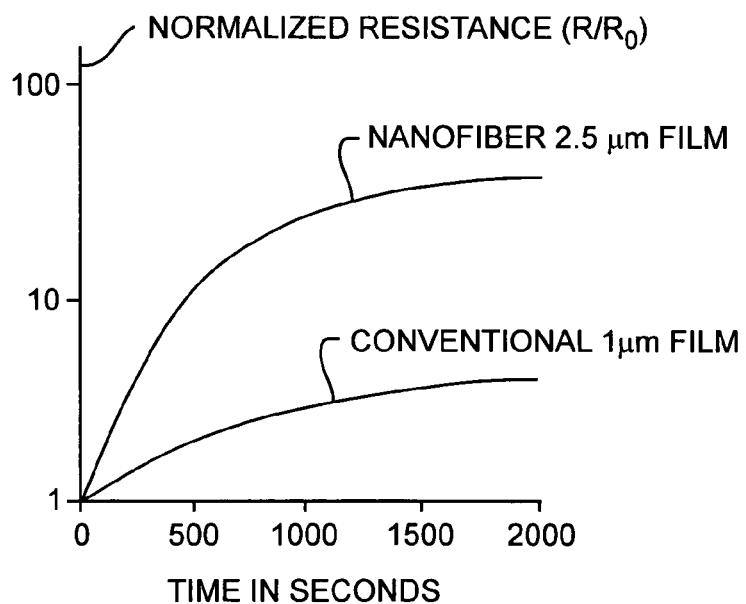
FIG. 4B is a graph of polyaniline nanofiber time response to a base dedopant.

Referring to FIGS. 1A, 1B, 2, 3, 4A, and 4B, and more particularly to FIGS. 4A and 4B, polyaniline nanofibers exhibit conductivity changes when dedoped or doped polyaniline nanofibers are exposed to an acid or when doped polyaniline nanofibers are exposed to a base. In the exemplar case, when camphorsulfonic acid is used in the catalysis solution, the polyaniline nanofibers have camphorsulfonic acid molecules are tightly incorporated within the polyaniline during the in-situ polymerization of aniline. Dedoped polyaniline nanofibers can be obtained by dialyzing the camphorsulfonic acid doped polyaniline against 0.1 M ammonium hydroxide, which produces the emeraldine base form of polyaniline. Once the camphorsulfonic acid molecules are removed, thin-film sensors made of dedoped fibers respond to repeated doping and dedoping. The sensor performance of the nanofibers having a predetermined size diameter distribution, can be measured using a dedoped nanofiber emeraldine base thin film, such as a 2.5 µm thick thin film as compared to a conventional dedoped thin film, such as a 1 µm thick thin film that can be deposited on an array of interdigitated gold electrodes. The sensor is exposed to an acidic dopant, such as hydrochloric acid, for acidic doping, and, then exposed to a base, such as ammonia, for basic dedoping. The sensor, for example, may consist of fifty pairs of electrodes at 4970×20×0.18 µm on a glass substrate with interdigitated gaps of 10 µm. The polyaniline nanofiber sensors then exhibit a fast, predetermined reaction time during both doping for acid vapor detection and dedoping for basic vapor detection. The conducting polyaniline nanofibers possess fast predetermined doping and dedoping times that are suitable for sensor applications.

The real time resistance changes of a dedoped film can be monitored using an electrometer upon exposure to an acid, such as 100 ppm of hydrochloric acid HCl, as shown in FIG. 4A, and of a fully HCl doped film exposed to a base, such as 100 ppm of ammonia $NH_3$, as shown in FIG. 4B. The resistance changes of a nanofiber emeraldine base thin film and conventional thin film upon exposure to 100 ppm HCl vapor and HCl doped films exposed to 100 ppm $NH_3$ vapor are shown. The $R/R_0$ ratio is the resistance R normalized to the initial resistance $R_0$ prior to gas exposure. The nanofiber thin film responds faster than a conventional film to both acid doping and base dedoping even though the nanofiber film is more than twice as thick. This is due to the small, predetermined diameter size of the nanofibers that provides a high surface area within the film that can be rapidly accessed by the gas vapors. Also, the small, predetermined diameters of the fibers allow gas molecules to diffuse in and out of the fibers in a much shorter predetermined amount of time. This also leads to a much greater extent of doping or dedoping over short times for the nanofiber films.

Films of doped nanofiber and conventional polyaniline can be measured and compared in response to exposure to alcohol vapors, such as methanol, ethanol, and propanol, or to water vapor. The mechanism of response in the case alcohol or water exposure is not doping or dedoping but rather conformational changes of the polymer film. The conformational changes produce a resulting change in conductivity for use as an alcohol or water vapor sensor. Again, the nanofiber sensor has a greater response with a faster response time. In the case of volatile organic chemicals, the response mechanism is swelling of the polymer both in bulk film and in nanofiber forms. The swelling also causes a resulting change in electrical conductivity, which can be used to sense the organic vapor. Reducing agents such as hydrazine react with polyaniline nanofibers to cause a change in oxidation state and a corresponding change in electrical conductivity and can be used to sense hydrazine. The nanofibers can also react with chemical vapors with a change in optical absorption qualities that can be detected using coated optical detectors in the chemical sensors. In all cases, the nanofiber films have improved sensor performance in both sensitivity magnitude and time response as compared to conventional bulk films for a range of analytes.

Figure 5:
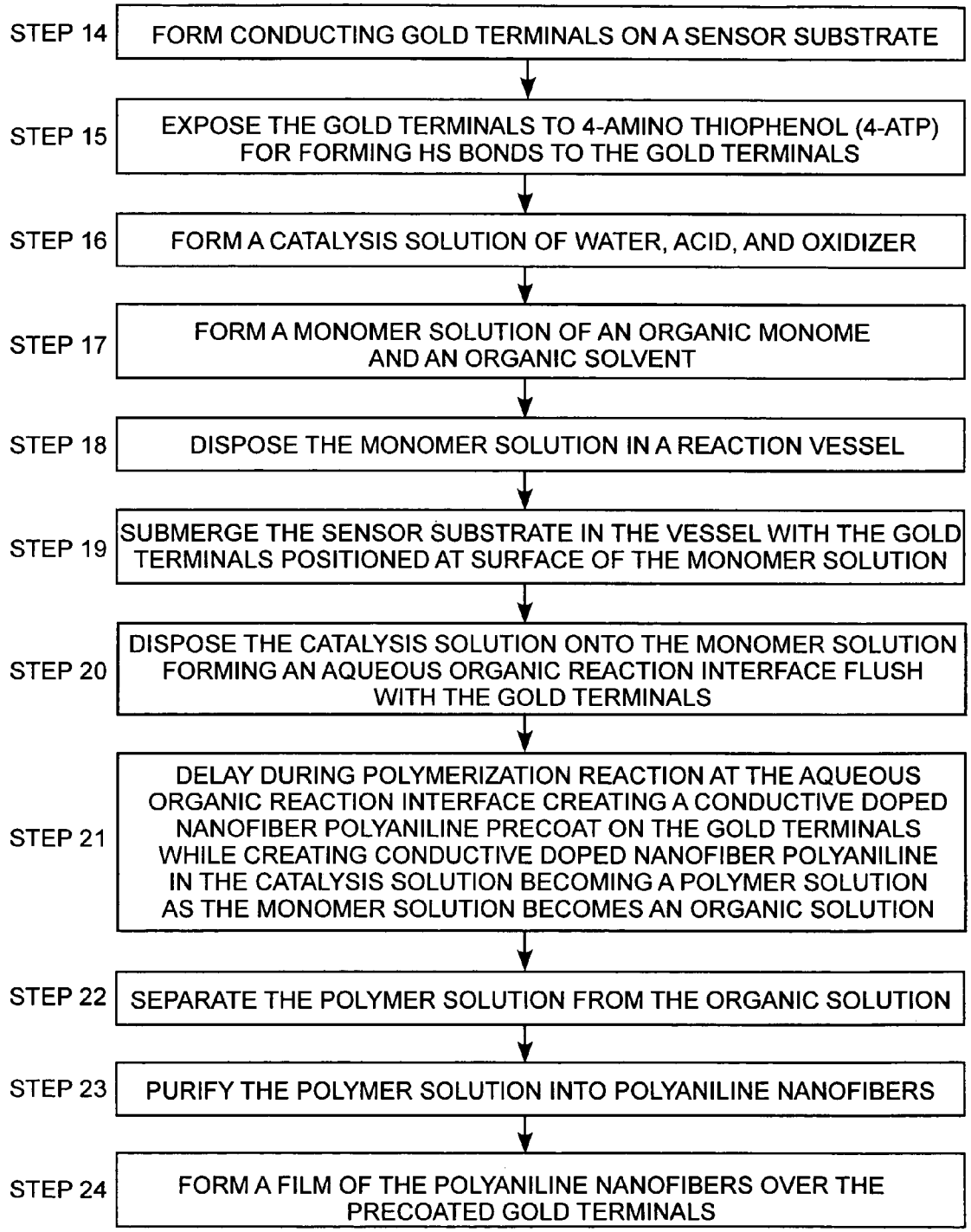
FIG. 5 is a process flow of a method for forming a polyaniline nanofiber precoated sensor.

Referring to FIG. 5, an enhanced sensor can be made by precoating the gold terminal of a sensor with polyaniline prior to a thin film in a method described in steps 14 through 24. In step 14, conducting gold terminals are disposed on a sensor substrate. In step 15, the gold terminals are exposed to 4-Amino Thiophenol (4-ATP) for forming a thiol RSH surface layer on the gold terminals. In step 16, the catalysis solution is formed of water, acid, and oxidizer. In step 17, the monomer solution is formed of the monomer and an organic solvent. In step 18, the monomer solution is disposed in a reaction vessel. In step 19, the sensor substrate is submerged in the vessel with the gold terminals positioned at the surface of the monomer solution. In step 20, catalysis solution is disposed onto the monomer solution forming an aqueous organic reaction interface flush with the gold terminals. A precoating of polyaniline nanofibers is formed over upon the thiol RSH surface layer while polyaniline nanofibers are also formed at the interface and dispersed into the catalysis solution. In step 21, the polymerization reaction is continued at the aqueous organic reaction interface creating conductive, doped polyaniline nanofibers that precoat the gold terminals while creating conductive, doped nanofiber polyaniline in the catalysis solution then becoming a polymer solution as the monomer solution becomes an organic solution. Alternatively, the polymerization reaction can also be continued to create a polyaniline nanofiber film that results in a conducting nanofiber film that spans electrodes to provide a complete chemical sensor after washing of the resulting film. In step 22, the polymer solution is separated from the organic solution, while the precoated substrate is removed from the vessel. In step 23, the polymer solution is purified into polyaniline nanofibers. In step 24, a film of the polyaniline nanofibers is disposed over the precoated gold terminals for forming a precoated sensor as shown in FIG. 6.

Figure 6:
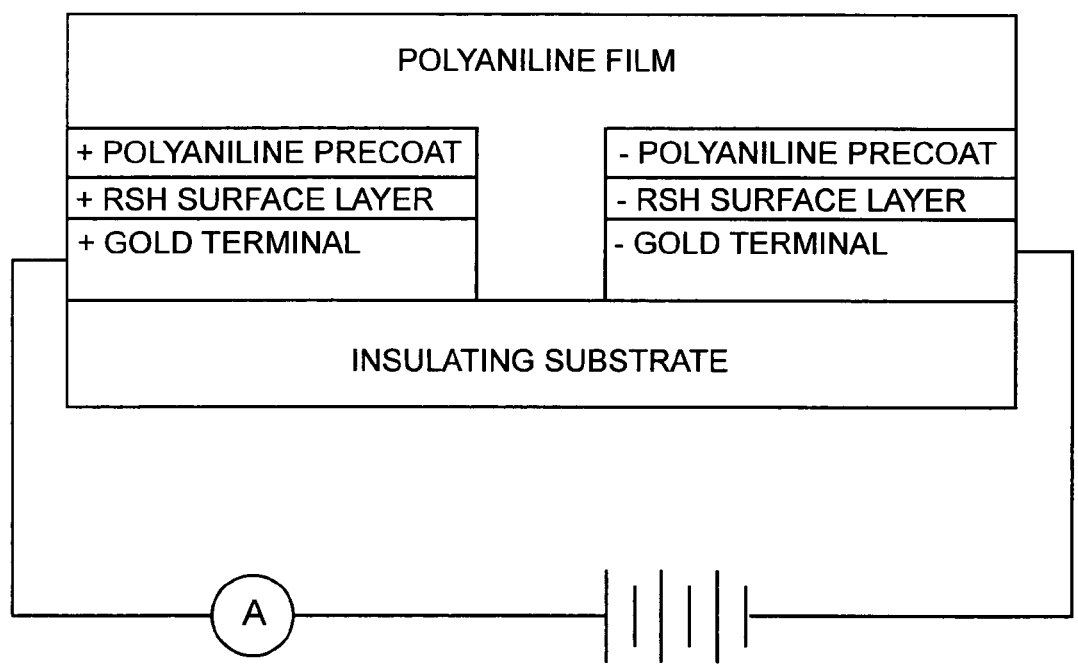
FIG. 6 is a block diagram of a polyaniline nanofiber precoated sensor.

Referring to FIG. 6, a polyaniline nanofiber precoated acid sensor includes the insulating substrate, at least two gold terminals, including a positive gold terminal and a negative gold terminal, upon both of which is disposed a thiol (RSH) film and a polyaniline precoat. Over the precoated gold terminals is disposed the thin film of polyaniline nanofibers. The precoating offers enhanced adherence and contact conductivity between the gold terminals and the polyaniline film. When the polyaniline film is exposed to a chemical vapor, the conductivity of the polyaniline film changes producing changes in resistivity that would then produce a change in electrical current as measured by a current meter that is connected in series with a DC power source that is in turn connected across the positive and negative gold terminals.

Referring to all of the figures, the synthesis method is based on the chemical oxidative polymerization of a monomer, such as aniline, in a strongly acidic catalysis solution having an acid component, such as camphorsulfonic acid, and an oxidant, such as ammonium peroxydisulfate. The polymerization is performed in an immiscible organic-aqueous biphasic system, in order to separate the by-products, including inorganic salts, and oligomers, according to solubility in the organic and aqueous phases. In an exemplar synthetic process, aniline is dissolved in an organic solvent, such as $CCl_4$, benzene, toluene, or $CS_2$ while ammonium peroxydisulfate is dissolved in water with camphorsulfonic acid. The two solutions are transferred into a reaction polymerization vessel for generating an interface between the two solutions. After a short period, such as a few minutes, green polyaniline forms at the interface and then gradually diffuses and disperses into the aqueous phase of the catalysis solution. After an extended period, such as several hours, the entire water phase is homogeneously filled with dark green polyaniline, while the lower organic layer appears red-orange, due to the formation of aniline oligomers. The aqueous phase is then collected and the by-products are removed by dialysis against deionized water, using for example, tubing with a 12K to 14K cutoff. When a deionized water bath reaches a pH of 7, a 10-µl suspension is diluted with 1 ml of deionized water. Dedoped polyaniline can then be obtained by dialysis using 0.1 M ammonium hydroxide and then deionized water. The synthetic method produces yields ranging from six to ten weight percent of nanofibers. Thin film sensors made of the polyaniline nanofibers have superior performance in both sensitivity and time response to a variety of gas vapors including acids such as hydrochloric, hydrofluoric, sulfuric, and nitric, bases such as ammonia and butylamine, and alcohols such as methanol, ethanol, and propanol. Thin film sensors made of the polyaniline nanofibers are also sensitive to some volatile organics such as chloroform and nitromethane, and to redox agents such as hydrazine.

The aqueous and organic interfacial synthesis of polyaniline nanofibers has several advantages. Both the synthesis and purification steps are template free. Uniform nanofibers are obtained in high yields. The synthesis method is scalable and reproducible with predetermined reactions and response times. Multiple syntheses performed from millimolar to molar quantities produce nanofibers of the same morphology, size distribution and uniformity. The nanofibers are readily dispersed in water, which facilitates environmentally friendly processing and biological applications. The nanofiber sensors have shorter doping and dedoping times with greater response to acidic and basic gases. The nanofiber sensors have a faster and larger response to alcohol vapors and react to some volatile organics and redox agents. Chemical sensors made from the nanofibers respond with larger magnitudes and faster response times to a wide range of analytes, and are well suited for chemical sensor applications.

The present invention is generally directed to a synthesis method for forming polymer nanofibers. When the polymer nanofibers are conductive, the resulting thin film can be used in a chemical sensor. Conducting polymer nanofibers include polyaniline nanofibers, polypyrrole nanofibers, and polythiophene nanofibers all of which can be used in chemical sensors. The method relies on the use of a monomer solution comprising an organic monomer and an organic solvent, and the use of a catalysis solution comprising an acid and an oxidizer, for producing at an aqueous and organic interfacial interface polymer nanofibers that preferably react to vapor exposures for suitable use in chemical sensors. Various monomers, solvents, oxidizers, and acids can be used as alternatives, modifications, and improvements to the preferred forms. Those skilled in the art can make enhancements, improvements, and modifications to the invention, and these enhancements, improvements, and modifications may nonetheless fall within the spirit and scope of the following claims.

What is claimed is:

1. A sensor for sensing the presence of a chemical vapor, the sensor adapted for interconnecting to an electrical monitor for measuring a reaction of the sensor to the chemical vapor, the sensor comprising, a positive terminal, the positive terminal being conductive, a negative terminal, the negative terminal being conductive, the terminals adapted for interconnection to the electrical monitor, and a film of organic conductive polymer nanofibers extending between the positive and negative terminal for producing a change in conductivity between the positive terminal and the negative terminal as monitored by the electrical monitor when the film is exposed to the chemical vapor, wherein the positive terminal and the negative terminal are made of gold and the conducting polymer is polyaniline, the sensor further comprising, a thiol surface layer disposed between the terminals and the film.

* * * * *